(12) United States Patent
Klimant

(10) Patent No.: US 7,456,023 B2
(45) Date of Patent: *Nov. 25, 2008

(54) REAGENT FOR LUMINESCENCE OPTICAL DETERMINATION OF AN ANALYTE

(75) Inventor: Ingo Klimant, Mintraching (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 681 days.

This patent is subject to a terminal disclaimer.

(21) Appl. No.: 10/451,958

(22) PCT Filed: Dec. 21, 2001

(86) PCT No.: PCT/EP01/15185

§ 371 (c)(1), (2), (4) Date: Apr. 19, 2004

(87) PCT Pub. No.: WO02/054045

PCT Pub. Date: Jul. 11, 2002

(65) Prior Publication Data

US 2004/0175836 A1    Sep. 9, 2004

(30) Foreign Application Priority Data

Dec. 29, 2000  (AT) ............................. A 2161/2000

(51) Int. Cl.
*G01N 21/00* (2006.01)
(52) U.S. Cl. ..................................... 436/164
(58) Field of Classification Search ............... 436/164
See application file for complete search history.

(56) References Cited

U.S. PATENT DOCUMENTS

| | | | | |
|---|---|---|---|---|
| 4,457,977 | A | * | 7/1984 | Walles ........................ 428/463 |
| 4,868,103 | A | * | 9/1989 | Stavrianopoulos et al. ..... 435/5 |
| 5,194,393 | A | | 3/1993 | Hugl et al. .................. 436/525 |
| 5,585,235 | A | | 12/1996 | Brocia ........................... 435/4 |
| 5,952,491 | A | * | 9/1999 | Leiner et al. ................. 540/467 |
| 7,067,320 | B2 | * | 6/2006 | Klimant ........................ 436/74 |

FOREIGN PATENT DOCUMENTS

| | | |
|---|---|---|
| EP | 0381026 A2 | 8/1990 |
| WO | WO 00/42438 | 7/2000 |
| WO | WO 02/054076 A2 | 7/2002 |

* cited by examiner

*Primary Examiner*—Walter D Griffin
*Assistant Examiner*—Bobby Ramdhanie
(74) *Attorney, Agent, or Firm*—Dinsmore & Shohl LLP

(57) ABSTRACT

The invention relates to a reagent for carrying out assays in accordance with the FRET-principle, containing an acceptor dye as well as particles exhibiting a donor dye, whereby the donor dye and the acceptor dye are located in different chemical phases, the acceptor dye is provided as bound to the particles and the particles are essentially impermeable to the sample medium or to components of the sample medium affecting the luminescence characteristics of the donor dye. The invention furthermore relates to a method for the qualitative and/or quantitative determination of at least one analyte and/or component of a liquid measuring medium, comprising the addition of the reagent according to the invention to the measuring medium.

10 Claims, 1 Drawing Sheet

REAGENT FOR LUMINESCENCE OPTICAL DETERMINATION OF AN ANALYTE

BACKGROUND OF THE INVENTION

The invention relates to a luminescence-optical method for qualitative and quantitative determination of at least one analyte and/or component of a liquid measuring medium containing a chromophore (or a luminophore) which is directly or indirectly responsive to the component to be determined by changing its absorption spectrum, and a luminophore which is not responsive to the component to be determined, where there is at least partial overlap between the emission spectrum of the luminophore and the absorption spectrum of the chromophore, and where the nonradiative energy transfer between luminophore and chromophore produces a measurable change in at least one luminescence characteristic of the luminophore. That principle is known as the so-called FRET-principle.

The invention further relates to a reagent for quantitative determination of at least one analyte and/or component of a gaseous or liquid measuring medium containing a chromophore (or a luminophore) which is directly or indirectly responsive to the component to be determined by changing its absorption spectrum, and a luminophore which is not responsive to the component to be determined, where there is at least partial overlap between the emission spectrum of the luminophore and the absorption spectrum of the chromophore, and where the nonradiative energy transfer between luminophore and chromophore produces a measurable change in at least one luminescence characteristic of the luminophore.

In the following, luminophores are understood as dyes which emit phosphorescence or fluorescence radiation upon suitable excitation. The absorption spectrum of the chromophore is influenced either directly by the component to be measured or indirectly by a chemical reaction product of the component to be measured. The term "quantitative determinations of a chemical component" refers to the determination of concentration and activity as well as gas partial pressure, the values of at least one luminescence characteristic of the luminophore being used to infer the measured quantity.

A method and a sensor in which pH- and cation-sensitive chromophores (acceptor) are attached, preferably covalently, to a luminophore (donor) are known from U.S. Pat. No. 5,232,858. The pH-value and/or concentration of the cation to be determined in the measuring medium is derived from the luminescence decay time of the luminophore.

As far as the state of the art is concerned, U.S. Pat. No. 5,648,269 is also to be mentioned. This document suggests the application of the apparent luminescence decay time of the luminophore for determining the measured quantity. With luminophores with one decay time component, the apparent luminescence decay time is identical with the effective decay time. With luminophores with several decay time components, it is easier to evaluate the apparent decay time, however—in particular with systems that are not robust—there is the drawback of increasing errors.

Luminescence decay times may be obtained by means of phase-modulation or time-resolved luminescence measuring techniques, respectively.

A similar method is known from EP-A-0 214 768. Therein, the concentration of the parameter to be determined in the measuring medium is inferred from the luminescence intensity measured.

The rate of nonradiative energy transfer from donor to acceptor molecules depends on the spatial proximity of the molecules of the two substances. The transfer rate $k_T(r)$ is extremely responsive to the spatial distance r between donor and acceptor and decays with the sixth power of the distance $$k_T(r) = \frac{1}{\tau_D}\left(\frac{R_O}{r}\right)^6,$$

whereby $\tau_D$ indicates the luminescence decay time of the donor in absence of the acceptor and $R_O$ indicates the characteristic Förster distance. The latter is that donor-acceptor distance in which a 50% efficiency of the energy transfer is provided. Depending on the respective donor-acceptor pair, $R_o$ is between 2 and 9 nm.

Due to the nonradiative energy transfer from donor to acceptor molecules, the macroscopically determinable values of the luminescence-optical parameters (luminescence quantum efficiency, luminescence intensity, luminescence decay time) of the luminophore will undergo a particularly efficient change if a substantial number of molecules of the two substances are brought into close spatial contact with each other.

To obtain close spatial contact, U.S. Pat. No. 5,232,858 proposes a covalent bonding of donor and acceptor molecules. In EP-A-0 214 768 individual donor and acceptor molecules are covalently attached to the surface of a joint substrate, such as glass.

The covalent bonding of donor and acceptor molecules as described in U.S. Pat. No. 5,232,858 has the advantage that the mean spatial distance of donor/acceptor may be kept as constant as possible. However, it is a disadvantage that particularly great synthesis efforts are required to produce covalent bonds between desirable luminophores and suitable pH- or ion-sensitive chromophores.

Considerable efforts are also needed to covalently attach donor and acceptor molecules to the surface of a joint substrate (EP-A-0 214 768), which, above all, brings about the drawback that boundary surface phenomena impair the quality of the measured results.

Thus, in U.S. Pat. No. 5,942,189 and U.S. Pat. No. 6,046,055 it is suggested that the luminophore and the chromphore are ionic substances of differing electrical charges, which are present as ionic pairs in a matrix material that is permeable to the chemical component to be determined.

The use of long-lived luminophores (having luminescence decay times >100 ns, preferably >1 µs), such as exhibited, for example, by metal-ligand complexes, certain porphyrins and lanthanides, is of utmost importance to a general commercial application. Long-lived luminescence provided, the optoelectronic arrangements and components for the determination of the luminescance decay time and/or values to be derived therefrom (for example, mean luminescance decay time, phase angle) may be determined in a particularly inexpensive manner by means of phase or time-resolved methods.

However, the inventor of the present application has recognized that the above-mentioned, previously known methods bring about the mutual disadvantage that in particular the luminescence of long-lived luminophores is influenced by a number of components of the measuring medium. A known characteristic of such luminophores is the particularly great dependency of the luminescence characteristic on the $O_2$ content of the sample. Consequently, such luminophores are thus often used for determining the $O_2$ content (EP-A-0 907 074). When using those luminophores as donor dyes with sensors based upon the FRET-principle, it is thus necessary to exactly know or determine the $O_2$ content of the measuring medium and to carry out appropriate adjustments. Examples of further substances having an influence on the luminescence quantum efficiency are amines and water. In the course of continuous measurements (monitoring), luminescence dyes may be completely or partially destroyed by the emerging singlet-$O_2$. Accordingly, additives for limiting that process were suggested. However, a general drawback of known, advantageous luminescence dyes is the luminescence characteristics' sensitivity to minor changes of the chemical-physical microenvironment, caused by any components of the sample, in particular water. In case of sample media of unknown and/or variable chemical or biochemical compositions, that leads to a significant limitation of the measuring accuracy. For example, in medical diagnostics, reproducibilities of +/−5 milli-pH are expected in the field of blood-pH determination.

It is the object of the invention to improve luminescence-optical determination methods based upon the FRET-principle, which are based upon a luminophore (donor) and a chromphore (acceptor, indicator) reversibly binding the substance (analyte) to be determined or its reaction products, with regard to the susceptance to failure caused by components of the sample to be measured. Furthermore, particularly great chemical synthesis steps needed to obtain the spatial proximity of a substantial number of acceptor molecules and shielded donor molecules are to be avoided.

SUMMARY OF THE INVENTION

According to the invention, this object is achieved in that the luminophore (donor) and the chromophore (acceptor) are located in different chemical phases. The matrix material of the donor phase is to be essentially impermeable to components of the sample medium affecting the luminescence characteristics of the donor. The matrix material of the acceptor phase is to be permeable to the analyte or its reaction products, respectively.

Thus, the invention relates to a reagent for carrying out assays in accordance with the FRET-principle, containing an acceptor dye as well as particles exhibiting a donor dye, whereby the donor dye and the acceptor dye are located in different chemical phases, the acceptor dye is provided as bound to the particles and the particles are essentially impermeable to the sample medium or to components of the sample medium affecting the luminescence characteristics of the donor dye.

Thus, the matrix material of the donor phase is provided so as to be dispersed in the form of small particles in the substance to be analyzed, with the acceptor molecules being bound at the surface of the particles.

Thereby, the chromophore may be bound at the surface adsorptively or electrostatically or, most preferably, covalently to functional groups.

In a preferred embodiment, unplasticized polymers such as polyacryl nitrile and its derivatives, PVC and/or polyvinylidene chloride are used as materials for the particles containing the donor dye.

The method according to the invention for the qualitative and/or quantitative determination of at least one analyte and/or component of a liquid measuring medium comprises the addition of the reagent according to the invention to the measuring medium.

Thus, only the particles containing the donor dye with the acceptor dye being bound to the particles has to be added to the measuring medium, f.i. in a measuring cuvette, whereupon the respective analysis is carried out in a manner known per se. Thus, the measuring medium is at the same time also the acceptor phase.

Preferably, the method according to the invention is used for the determination of the pH-value of a sample or for the determination of concentrations and/or activities of ions, in particular $Li^+$, $Na^+$, $K^+$, $Mg^{++}$, $Ca^{++}$ or $Cl^-$, in a sample.

Further areas of application of the method according to the invention concern so-called transducers. Therein, the chromophore does not directly react with the analyte, but indirectly. Examples of that are so-called enzymatical sensors (for example, for determining urea and creatinine). Thereby, one or more enzymes react with the analyte, leading to the formation of a product which reacts directly with the chromophore.

Preferably, the measuring medium is a body fluid, in particular blood, plasma or serum.

Most advantageous luminophores (donor) used according to the invention are those which feature high luminescence quantum efficiency and long luminescence decay time (>100 ns). Preferred luminophores are cationic, metalorganic complexes of palladium, rhodium, platinum, ruthenium, osmium, rare earths (in particular, europium and lanthanum). The organic portion of these metalorganic complexes may consist, for example, of ligands from the group of porphyrins, bipyridyls, phenanthrolines or other heterocyclical compounds.

Preferred pH- and cation-sensitive chromophores (acceptor) are anionic substances whose light absorption will change upon direct or indirect chemical/physical interaction with the component of the sample medium to be determined, and whose absorption spectrum overlaps the emission spectrum of the luminophore, at least partially.

DETAILED DESCRIPTION

Figure 1:
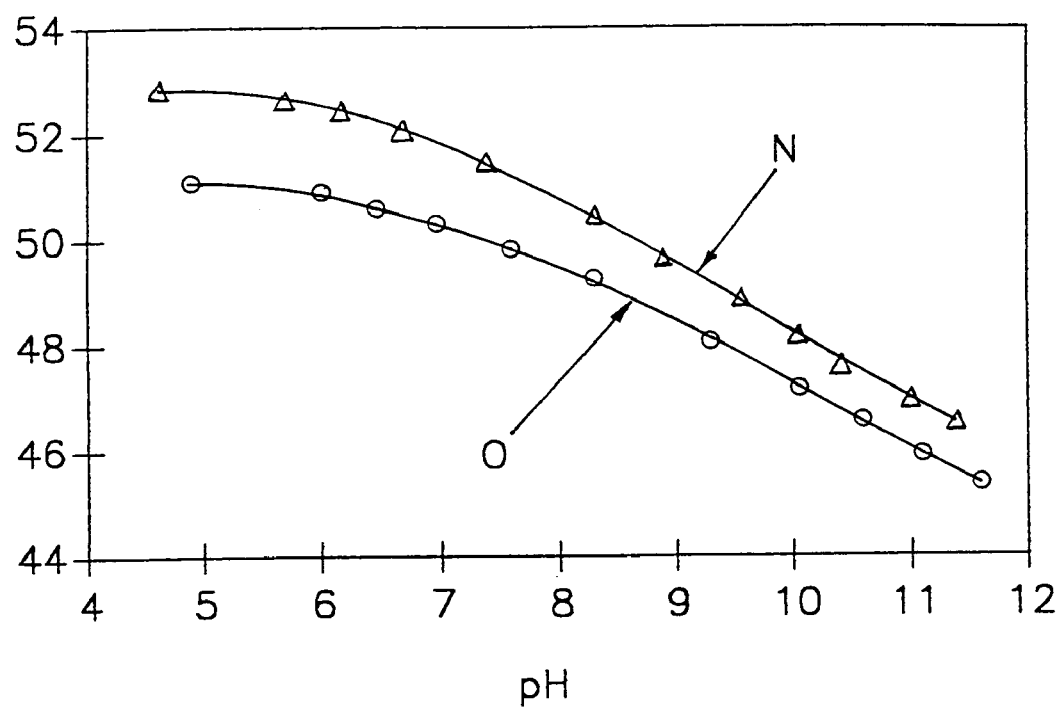
FIG. 1 shows the calibration curve of an optical reagent based upon the FRET-principle (produced in accordance with section 2.3 of the example part) and containing a pH-sensitive acceptor dye, the donor dye being present "in protected fashion" in a donor phase of the invention (particles). The two curves show the phase angle (ordinate) of the luminescence light of the pH reagent dispersed in calibration liquids exhibiting differing pH-values (abscisse). The curve denoted by "O" was taken up when being saturated by air (21.95% $O_2$). The curve denoted by "N" was taken up when being saturated by $N_2$.

I) Determination of the pH-Value of a Sample

Optical sensors for pH determination according to the state of the art (cf M. J. P. Leiner and O. S. Wolfbeis "Fiber Optic pH Sensors" in O. S. Wolfbeis "Fiber Optic Chemical Sensors and Biosensors", CRC-Press, Boca Raton, 1991, Vol. 1, Chapter 8) usually contain an absorption dye (chromophore) or fluorescent dye incorporated in an ion-permeable, preferably hydrophilic polymer matrix. In dependence of the pH-value (pH=−log(aH+)) of the sample medium, a thermodynamic equilibrium is established between the protonated and deprotonated forms of the chromophore or fluorophore, respectively. From the concentration ratio of the two forms measurable by optical methods, the pH-value of the sample medium may be obtained.

Reaction:

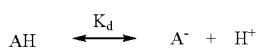

Equilibrium $$K_d = \frac{cA^- * cH^+}{cAH}$$

AH is the protonated, and A⁻ is the deprotonated form of the pH-sensitive Chromophore. H⁺ denotes a proton. $K_d$ is the equilibrium constant. c denotes the concentration.

In U.S. Pat. No. 5,232,858 initially mentioned, pH-sensitive chromophores are described, which are attached, preferably covalently, to a pH-insensitive luminophore (donor). From the luminescence decay time of the luminophore (L), the pH-value of the test solution is obtained.

For luminescence-optical pH-determination according to the invention, for example, a pH-sensitive chromophore is used as an acceptor dye, which is provided in the acceptor phase or is at least in direct contact with the acceptor phase, respectively, whereby the acceptor phase is the medium to be analyzed (measuring medium).

In the instance of low pH-values (pH<<pK of the chromophore) of the sample medium, the chromophore is present in fully protonated form. Due to the minimal spectral overlap of the absorption band of the deprotonated chromophore and the emission band of the luminophore, the nonradiative energy transfer rate from luminophore to chromophore reaches a minimum. Correspondingly, the values of mean luminescence decay time and relative luminescence intensity of the luminophore reach a maximum.

In the instance of high pH-values (pH>>pKa of the chromophore) of the sample medium, the chromophore is present in fully deprotonated form. Due to the maximal spectral overlap of the absorption band of the deprotonated chromophore and the emission band of the luminophore, the nonradiative energy transfer rate from luminophore (donor, donor dye) to chromophore (acceptor, acceptor dye) reaches a maximum. Correspondingly, the values of mean luminescence decay time and relative luminescence intensity of the luminophore reach a minimum.

For pH-values of the sample medium in the range of +/−1.5 pH units of the pKd value (pKd=−log Kd) of the chromophore, the pH-value of the sample medium may be inferred with sufficient accuracy from the mean luminescence decay time or relative luminescence intensity of the luminophore.

II) Determination of Concentrations and/or Activities of Cations and Anions in a Sample (Li⁺, Na⁺, K⁺, Mg⁺⁺, Ca⁺⁺, Cl−

Previously known optical sensors and optical measuring methods, respectively, for determining the concentrations and/or activities of cations in a sample medium are based upon different methods. U.S. Pat. No. 5,232,858 as initially mentioned describes cation-sensitive chromphores (chromoionophores) which are attached, preferably covalently, to a cation-insensitive luminophore.

In the instance of very high cation concentrations ($cY^{+p}$>>Kd of the chromophore) of the sample medium, the chromophore is present in fully complexed form. (Y is the cation to be determined, +p is its atomic number.) In the instance of very low cation concentrations ($cY^{+p}$<<Kd of the chromophore) of the sample medium, the chromophore is present in free, noncomplexed form.

If the logarithmic concentration $\log(cY^{+p})$ of the cation to be determined of the sample medium is in the range of −log (Kd)+/−10.5, the concentration of the cation to be determined in the sample medium may be inferred with sufficient accuracy from the mean luminescence decay time and/or relative luminescence intensity of the luminophore.

pH-sensitive chromophores used according to the invention are exemplified in Table 1 below:

TABLE 1

| pH-sensitive chromophores | | |
|---|---|---|
| Chromophore | Absorption wavelength [nm] protonated/deprotonated | pKa |
| Triphenylmethane dyes: | | |
| Bromophenol blue | 430/617 | 3.8 |
| Bromothymol blue | 430-435/615-618 | 6.7 |
| Dibromoxylenol blue | 420/614 | 7.6 |
| Azo dyes: | | |
| Calmagit | 530/605 | 8.0 |
| Nitrazine yellow | 460/590 | 6.5 |
| Others: | | |
| o-chlorophenol-indophenol | 555/625 | 7.1 |
| Naphthol-phthalein | 428/661 | 6.7, 7.9 |

In addition, pH-sensitive triphenylmethane dyes of the general form

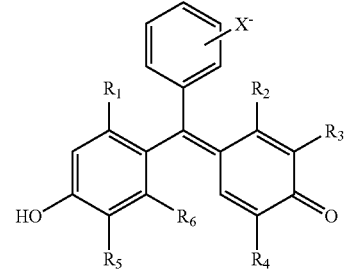

are used. Independently of each other, R1-6 may be H, halogen atoms, nitro groups and alkyl groups. X⁻ stands for an optional group for covalently immobilizing the chromophore. Suitable groups are, for example —(CH$_2$)$_n$—SO3⁻ or —(CH$_2$)$_n$—COO⁻, —(CH$_2$)$_n$—NH$_2$ (n=0-18).

pH-sensitive azo dyes of the general form

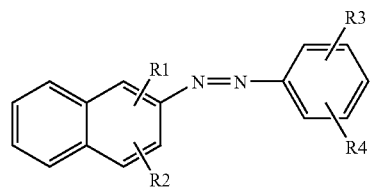

wherein, independently of each other, R1-R4 stand for substitutes, such as halogen atoms, nitro groups or alkyl groups, respectively, and groups suitable for covalent immobilization, whereby, however, at least one —OH group has to be present.

Cation-Sensitive Chromophores Suitable for Use According to the Invention:

Examples of cation-sensitive chromoionophores usable according to the invention for the determination of lithium, potassium, sodium, magnesium and calcium ions include anionic azo dyes, stilbene dyes and merocyanines, which contain at least one ion-selective group (ionophore group) and whose absorption band with the longest wavelengths overlaps the emission band of the luminophore at least partially, the interaction with the cations to be determined leading to a spectral shift of the absorption band with the longest wavelengths.

TABLE 2

Luminophore (donor dyes)

| Luminophore (L) | Abbrev. | Absorption maximum (nm) | Luminescence maximum (nm) |
|---|---|---|---|
| $(Ru(II)\text{-tris-}2,2'\text{-bipyridyl})^{2+}$ | $Ru(bpy)_3^{2+}$ | 452 | 628 |
| $(Ru(II)\text{-tris-}2,2'4,4\text{-diphenyl bipyridyl})^{2+}$ | $Ru(dph\text{-}bpy)_3^{2+}$ | 474 | 632 |
| $(Ru(II)\text{-tris-}1,10\text{-phenanthroline})^{2+}$ | $Ru(phen)_3^{2+}$ | 447 | 604 |
| $(Os(II)\text{-bis-terpyridine})^{2+}$ | | 510 | 729 |
| $(Os(II)\text{-tris-}1,10\text{-phenanthroline})^{2+}$ | | 650 | 690 |

Other central atoms used are Ir, Rh, Pd, Pt or Re.

In the following, the invention will be explained in greater detail with reference to FIG. 1, wherein FIG. 1 shows a calibration curve of a reagent according to the invention for pH-determination.

Determination of Calibration Values:

The determination of the calibration curves (FIG. 1) and the $O_2$ dependencies was carried out by determining the phase shift of the luminescence with regard to the excitation light modulated in sinusoidal fashion. Due to the use of a long-lived luminophore, a simple measuring arrangement exhibiting a modulation frequency of 45 kHz is sufficient. For the purpose of measuring, sensor disks were punched from the sensor foils, they were attached to the end piece of a two-armed light guide bundle and were contacted with the respective measuring media, or the end piece of the light guide bundle was dipped directly into the measuring medium containing the sample. A blue LED (470 nm) supplied with an amplitude voltage of 5V, which had been modulated up to 45 kHz in sinusoidal fashion, was used as an excitation light source. Blue foil filters were used as filters for the excitation light. The excitation light was guided to the sensor foil or to the test liquid, respectively, by means of light guides. The emitted luminescence light was guided to a filter, a combination of a OG 570 glass filter (Schott) and a red foil filter, by means of a light guide bundle and was further guided onto a detector (photo multiplier, type Hamamatsu H5702). The distribution voltage modulated in sinusoidal fashion of the LED and the signal of the detector were evaluated by means of a lock-in amplifier. The phase shift $\phi$ was obtained as a measuring signal. The decay time $\tau$ was calculated from the measured phase shift $\phi$ and the modulation frequency f=45 kHz according to the following formula: $\tau=\tan(\phi)/(2\pi f)$.

Phosphate buffers which had been adjusted to the desired pH-values with the aid of NaOH or HCl, respectively, were used as measuring and/or calibration media for the pH reagent (FIG. 1). The buffers were adjusted to the atmospheric oxygen value by employing tonometrics with air or were rendered oxygen-free by adding $Na_2SO_3$.

FIG. 1 shows the calibration curve of an optical reagent based upon the FRET-principle (produced in accordance with section 2.3 of the example part) and containing a pH-sensitive acceptor dye, the donor dye being present "in protected fashion" in a donor phase of the invention (particles). The two curves show the phase angle (ordinate) of the luminescence light of the pH reagent dispersed in calibration liquids exhibiting differing pH-values (abscisse). The curve denoted by "O" was taken up when being saturated by air (21.95% $O_2$). The curve denoted by "N" was taken up when being saturated by $N_2$.

EXAMPLES $Ru(diphphen)_3TMS_2Ru(II)$-tris-(4,7-diphenyl-1,10-phenanthroline) (3-trimethylsilyl)-1-propane sulphonate] (I. Klimant and O. S. Wolfbeis, Anal. Chem. 67 (1995) 3160).

Example 1

This example shows that a donor dye which, according to the invention, is embedded in a donor phase exhibits less $O_2$ sensitivity than the same dye being embedded in the acceptor phase.

General Description of the Preparation of Nanoparticles with Embedded Donor Dye.

1.1 Embedding of a Donor Dye into an Acceptor Phase 1 mg of donor dye $Ru(diphphen)_3TMS_2$ and 100 mg of the hydrophilic polymer D4 (polyurethane with hydrophilic sequences; Tyndale Plains Hunter LTD, Ringoes, N.J. 08551, USA) were dissolved in ethanol:water (90:10 w/w). The solution was drawn up a polyester foil (Mylar, Dupont) by knife application. After evaporation of the solvent, a film with a layer thickness of approximately 20 μm emerged.

Measuring Arrangement (45 kHz, Blue LED, OG 570)

| Dry: | air | 55.4° | $N_2$: | 58.3° |
|---|---|---|---|---|
| Water: | air saturated: | 53.5° | $N_2$ saturated: | 58.4° |

The measuring result shows that the donor dye $Ru(diphphen)_3TMS_2$ being present "in unprotected fashion" in an acceptor phase exhibits an $O_2$ sensitivity of 2.90 (dry acceptor phase) or of 4.9° (wet acceptor phase), respectively, when getting into contact with $O_2$-free ($N_2$ saturation) or 21.95% $O_2$ (air) saturated, gaseous and aqueous media.

1.2 Preparation of Nanoparticles with Donor Dye 400 mg polyacryl nitrile (Polyscience) and 8 mg $Ru(diphphen)_3TMS_2$ were dissolved in 80 ml DMF (Merck). After slowly dripping in 500 ml of water, the emerged suspension was mixed with NaCl and was centrifuged. The centrifuge effluent was washed with water several times and subsequently with ethanol.

1.3 Embedding of the Donor-Dye Carrying Nanoparticles into a Stratified Acceptor Phase The ethanolic suspension (of 1.2) was mixed with a solution of 400 mg of the hydrophilic polymer D4 (Tyndale Plains Hunter LTD, Ringoes, N.J. 08551, USA) in 5 ml ethanol:water (90:10 w/w). The suspension was drawn up a polyester foil (Mylar, Dupont) by knife application. After evaporation of the solvent, a film with a layer thickness of approximately 20 μm emerged.

Measuring Arrangement (45 kHz, Blue LED, OG 570)

| Dry: | air | 57.4°; | $N_2$: | 58.2° |
|---|---|---|---|---|
| Water: | air saturated: | 56.8° | $O_2$ free ($SO_3^{2-}$): | 58.6° |

The measuring result shows that the donor dye Ru(diphphen)$_3$TMS$_2$ embedded in a nanoparticle of the invention and thus being present "in protected fashion" in the donor phase exhibits an $O_2$ sensitivity of 0.8° (dry acceptor phase) or of 1.6° (wet acceptor phase), respectively, when getting into contact with $O_2$-free or 21.95% $O_2$ saturated, gaseous or aqueous media.

By comparing these values with the values of 1.1, it thus becomes apparent that one and the same donor dye which is present in a donor phase according to the invention exhibits less $O_2$ sensitivity than the donor dye which, according to the state of the art, is present directly in the acceptor phase.

Example 2

Reagent According to the Invention

General Description of the Preparation of pH Functional Nanoparticles and a pH-Sensitive Layer In a first step, a OH functional copolymer made up of acrylonitrile and an OH functional methacrylate is prepared. In a second step, nanoparticles containing an embedded donor dye are produced from that polymer. In a third step, a pH-sensitive acceptor dye is covalently attached to the functional groups of the copolymer. In doing so, the acceptor dye is located predominantly in the "soft" hydrophilic regions (acceptor phase) of the particles, thus being accesible for ions. The donor dye is dissolved predominantly in the "hard" regions (donor phase), thus making it difficult for interfering substances to gain access.

2.1 Preparation of the Copolymer 230 g de-ionized $H_2O$ were rendered oxygen-free by 2 h of rinsing with nitrogen. Under stirring and a nitrogen environment, 4 g SDS (sodium dodecyl sulphate p.A., Merck) were dissolved. 20 ml acrylonitrile (Fluka) and 1 ml polyethylene glycolmonometacrylate (Polyscience, n=200, order no. 16712) were added to that solution. That mixture was taken to 50° and mixed with 4 ml 1 N HCl (Merck). Polymerization was started by adding 400 mg ammonium peroxodisulphate (Merck) and was carried out for 12 h at 50°. The polymer was sucked off and washed several times with water and ethanol. In the following, this polymer is called PAN-PEG.

2.2 Preparation of Nanoparticles with Donor Dye 400 mg PAN-PEG and 20 mg of the donor dye Ru(diphphen)$_3$TMS$_2$ were dissolved in 80 ml DMF (Merck). After slowly dripping in 500 ml of water, the suspension was mixed with NaCl and was centrifuged. The centrifuge effluent was washed with water several times.

2.3 Binding of the pH-Sensitive Acceptor Dye of the Chromophore to the Nanoparticles 25 mg of the pH-sensitive acceptor dye N9 (Merck) were pulverized with 8 Tr. $H_2SO_4$ conc. (Merck) and were activated for 30 min in a water jet vacuum. The dye was absorbed in 100 ml of de-ionized water and was taken to pH 7 with the aid of NaOH. The above described centrifuge effluent was added to this mixture, after 5 min 4.2 g $NaCO_3$, and after 5 min 2 ml 5 M NaOH were added. After further 20 min, acidification to pH 3 by means of HCL conc. was carried out. The particles were split off by centrifugation and were washed with basic buffer, water and ethanol.

The thus produced particles were suspended into an aqueous measuring medium, and the measurements were carried out at various pH-values and unter air and $N_2$ saturation. The result is depicted in FIG. 1 and shows that, for the purpose of pH determination, the pH-sensitive particles may be added to the measuring medium as reagents (=engl. "probe"). Measuring medium: pH 7.3 Air saturated: 50.0° $O_2$-free (N2 saturated): 51.3°

The invention claimed is:

1. A reagent for qualitative and quantitative determination of at least one analyte in a liquid measuring medium in accordance with the FRET principle, wherein the reagent comprises particles impermeable to the liquid measuring medium and comprising a donor dye, wherein the donor dye defines an emission spectrum;

an acceptor dye bound to the surface of the particles covalently, electrostatically, or adsorptively, wherein the acceptor dye defines an absorption spectrum; and wherein the particles comprising the donor dye and the acceptor dye bound thereon are configured to be dispersed inside the liquid measuring medium, the donor dye being in sufficient spatial proximity to the acceptor dye to produce nonradiative energy transfer from molecules of the donor dye to molecules of the acceptor dye.

2. A reagent according to claim 1, wherein the particles comprise at least one unplasticized polymer.

3. A reagent according to claim 2, wherein the polymer is at least one of polyacryl nitrile, a derivative of polyacryl nitrile, PVC, and/or polyvinylidene chloride.

4. A method for the qualitative and/or quantitative determination of at least one analyte in a liquid measuring medium, comprising adding a reagent of claim 1 to the measuring medium;

determining the luminescence characteristics of the donor dye wherein the luminescence characteristics include luminescence decay time, luminescence intensity, or both; and inferring the analyte value of the liquid measuring medium from the luminescence characteristics of the donor dye.

5. A method according to claim 4, wherein the method determines the pH-value of the liquid measuring medium.

6. The method of claim 4, wherein the method determines at least one of the concentration or activity of an ion in the liquid measuring medium.

7. The method of 6 wherein the ion is $Li^+$, $Na^+$, $K^+$, $Mg^{++}$, $Ca^{++}$ or Cl.

8. The method of claim 4 wherein the liquid measuring medium is a body fluid.

9. A method for the qualitative and/or quantitative determination of at least one analyte in a liquid measuring medium comprising: adding a reagent of claim 1 to the measuring medium; and determining whether the acceptor is in complexed or noncomplexed form in order to determine the concentration of an ion in the liquid measuring medium, wherein a complexed acceptor form corresponds to a high ion concentration.

10. The method of claim 9 wherein the liquid measuring medium is a body fluid.

* * * * *